US011058749B2

(12) United States Patent
DiCosmo

(10) Patent No.: US 11,058,749 B2
(45) Date of Patent: Jul. 13, 2021

(54) BIOACTIVE COLLAGEN BIOMATERIALS AND METHODS FOR MAKING

(71) Applicant: Frank DiCosmo, Richmond Hill (CA)

(72) Inventor: Frank DiCosmo, Richmond Hill (CA)

( * ) Notice: Subject to any disclaimer, the term of this patent is extended or adjusted under 35 U.S.C. 154(b) by 0 days.

(21) Appl. No.: 15/140,885

(22) Filed: Apr. 28, 2016

(65) Prior Publication Data

US 2016/0317625 A1 Nov. 3, 2016

Related U.S. Application Data

(60) Provisional application No. 62/153,845, filed on Apr. 28, 2015.

(51) Int. Cl.
| | | |
|---|---|---|
| *A61K 38/39* | (2006.01) | |
| *A61L 15/32* | (2006.01) | |
| *A61L 27/24* | (2006.01) | |
| *A61L 15/60* | (2006.01) | |
| *A61L 15/42* | (2006.01) | |
| *A61L 27/56* | (2006.01) | |
| *A61L 27/36* | (2006.01) | |
| *A61L 27/54* | (2006.01) | |

(52) U.S. Cl.
CPC ............ *A61K 38/39* (2013.01); *A61L 15/325* (2013.01); *A61L 15/425* (2013.01); *A61L 15/60* (2013.01); *A61L 27/24* (2013.01); *A61L 27/3604* (2013.01); *A61L 27/54* (2013.01); *A61L 27/56* (2013.01); *A61L 2300/404* (2013.01)

(58) Field of Classification Search
CPC ..... A61K 38/39; A61L 15/325; A61L 15/425; A61L 15/60; A61L 2300/404; A61L 27/24; A61L 27/3604; A61L 27/54; A61L 27/56; A61P 17/02
See application file for complete search history.

(56) References Cited

U.S. PATENT DOCUMENTS

| | | | |
|---|---|---|---|
| 2,559,395 A | 7/1951 | Brown | |
| 4,394,370 A * | 7/1983 | Jefferies | A61L 27/227 106/122 |
| 4,412,947 A | 11/1983 | Cioca | |
| 4,703,108 A | 10/1987 | Silver et al. | |
| 4,948,540 A | 8/1990 | Nigam | |
| 4,970,298 A | 11/1990 | Silver et al. | |
| 6,309,454 B1 | 10/2001 | Harvey et al. | |
| 6,541,023 B1 | 4/2003 | Andre et al. | |
| 7,393,437 B2 | 7/2008 | Chan et al. | |
| 7,671,016 B2 | 3/2010 | Bouwstra et al. | |
| 8,354,123 B2 * | 1/2013 | Ditizio | A61K 9/7007 424/484 |
| 8,361,501 B2 * | 1/2013 | DiTizio | A61K 9/7007 424/484 |
| 8,628,800 B2 * | 1/2014 | DiTizio | A61K 9/7007 424/484 |
| 9,289,533 B2 * | 3/2016 | Schussler | A61L 27/38 |
| 2004/0028738 A1 | 2/2004 | Huang et al. | |
| 2007/0027414 A1 | 2/2007 | Hoffman et al. | |
| 2009/0253810 A1 * | 10/2009 | Katz | A61K 35/32 514/773 |
| 2010/0184183 A1 | 7/2010 | Schussler et al. | |
| 2010/0256774 A1 | 10/2010 | Wang et al. | |
| 2011/0097402 A1 | 4/2011 | Ditizio et al. | |
| 2011/0171180 A1 | 7/2011 | Bush et al. | |
| 2012/0121660 A1 * | 5/2012 | Akella | A61L 24/0063 424/400 |
| 2014/0276493 A1 * | 9/2014 | Leung | A61K 38/39 604/319 |

FOREIGN PATENT DOCUMENTS

EP          1153622 A1    11/2001

OTHER PUBLICATIONS

Anonymous "A Guide to Freeze Drying for the Laboratory" Labonco Corporation. Published 2010.*
Veljens L "Glycosaminoglycans of Human Bone Tissue" Calcified Tissue Research 7:175-190. Published 1970.*
Taubenberger et al. "The effect of unlocking RGD-motifs in collagen I on pre-osteoblast adhesion and differentiation" Biomaterials 31:2827-2835 (Year: 2010).*
Haugh et al. "The effect of dehydrothermal treatment on the mechanical and structural properties of collagen-GAG scaffolds" J. Biomed. Materials Res. 89A:363-369. (Year: 2009).*
Brett D "A Review of Collagen and Collagen-based Wound Dressings" Wounds Research 20:1-3 (Year: 2008).*
Grover et al. "Investigating the morphological, mechanical and degradation properties of scaffolds comprising collagen, gelatin and elastin for use in soft engineering" J. Mechanical Behavior of Biomedical Materials 10:62-74. (Year: 2012).*
Snejdrove E and Dittrich M "Pharmaceutically Used Plasticizers" Recent Advances in Plasticizers, Ed. M. Luquman, ISBN: 978-953-51-0363-9, InTech. (Year: 2012).*
Snyder et al. "Technology Assessment Skin Substitutes for Treating Chronic Wounds" Agency for Healthcare Research and Quality Technology Assessment Program. Technology Assessment Report Project ID: HCPR0610. (Year: 2011).*
Weadock et al. "Physical crosslinking of collagen fibers: Comparison of ultraviolet irradiation and dehydrothermal treatment" J. Biomed. Maters. Res. 29:1373-1379. (Year: 1995).*

(Continued)

*Primary Examiner* — Marcela M Cordero Garcia
(74) *Attorney, Agent, or Firm* — Marshall, Gerstein & Borun LLP

(57) ABSTRACT

A bioactive collagen biomaterial according to the invention that is biocompatible with cells and tissues and distinguished by containing certain cryptic and non-cryptic peptide constituents to stimulate cellular responses and further made to incorporate a variety of agents to provide a desired characteristic, such as antimicrobial properties. The bioactive collagen biomaterial can be provided as a variety of configurations and as various matrices and devices for use in medical applications such as in biotechnology, basic research, tissue engineering and in wound repair as a wound dressing or cell/tissue scaffold.

21 Claims, No Drawings

(56) References Cited

OTHER PUBLICATIONS

Drexler et al., Dehydrothermal crosslinking of electrospun collagen. *Tissue Eng. Part C: Methods* 17: 9-17 (2011).
Haugh et al. Crosslinking and mechanical properties significantly influence cell attachment, proliferation, and migration, within collagen glycosaminoglycan scaffolds. *Tissue Eng. Part A* 17(9-10): 1201-8 (2011).
Haugh et al., The effect of dehydrothermal treatment on the mechanical and structural properties of collagen-GAG scaffolds. *J. Biomed. Mater. Res. A.* 89(2): 363-9 (2009).
Hersel et al., RGD modified polymers: biomaterials for stimulated cell adhesion and beyond. *Biomaterials* 24: 4385-415 (2003).
Huveneers et al., Adhesion signaling—crosstalk between integrins, Src and Rho. *J. Cell Sci.* 122: 1059-69 (2009).
Liu et al., One-step derivation of mesenchymal stem cell (MSC)-like cells from human pluripotent stem cells on a fibrillar collagen coating. *Plos One* 7(3): e33225 (2012).
Niu et al., *J. Mater. Sci. Technol.* 21: 571-6 (2005).
Pedchenko et al., $\alpha v \beta 3$ and $\alpha v \beta 5$ integrins bind both the proximal RGD site and non-RGD motifs within noncollagenous (NC1) domain of the $\alpha 3$ chain of type IV collagen: implication for the mechanism of endothelia cell adhesion. *J. Biol. Chem.* 279: 2772-80 (2004).
Sinanan et al., $\alpha v \beta 3$ and $\alpha v \beta 5$ integrins and their role in muscle precursor cell adhesion. *Biol. Cell.* 100: 465-77 (2008).
Yannas et al., Biologically active collagen-based scaffolds: advances in processing and characterization. *Philos. Trans. A Math. Phys. Eng. Sci.* 368: 2123-39 (2010).

\* cited by examiner

BIOACTIVE COLLAGEN BIOMATERIALS AND METHODS FOR MAKING

RELATED APPLICATIONS

This application claims benefit of U.S. Provisional Application No. 62/153,845 filed on Apr. 28, 2015 the entire contents of which is incorporated herein by reference in its entirety and made a part of this application.

FIELD OF THE INVENTION

The present invention relates to a bioactive collagen biomaterial and methods of making. Further, the bioactive collagen biomaterial according to the invention is biocompatible. The bioactive collagen biomaterial can be provided as a variety of configurations and as various matrices and devices for use in medical applications such as in biotechnology, basic research, tissue engineering and in wound repair as a wound dressing or cell/tissue scaffold. The bioactive collagen biomaterial may be distinguished by containing certain cryptic and non-cryptic peptide constituents to stimulate cellular responses and further made to incorporate a variety of agents to provide a desired characteristic, such as antimicrobial properties.

BACKGROUND OF THE INVENTION

The extracellular matrix (ECM) is a complex structure in the body that surrounds and supports cells. In vivo, cells, including stem cells reside within the ECM, receive and respond to physical and biochemical signals from neighbouring cells, ECM components and tissues. The ECM consists of several structural proteins such as collagen, laminin, fibronectin, vitronectin, and elastin that are susceptible to degradation and reassembly. The most abundant of the ECM proteins is collagen.

Collagen and other structural proteins of the ECM are often associated with proteoglycans and glycoproteins. These molecules provide signaling that regulate cellular response and cell behavior. Cells bind to the ECM via integrins. Integrins link the internal cellular cytoskeleton to the external ECM through cytoplasmic bridging proteins, and mediate the cells' ability to sense the ECM-environment and respond accordingly. Increased or even reduced cell adhesion via integrins has determinative effects on cellular metabolism and function. It is now widely accepted that the ECM and collagen participate in regulation of the function of cells within the ECM. Interactions between cells and the extracellular matrix coordinate signaling pathways that control various aspects of cellular behavior. Integrins sense the physical properties of the extracellular matrix and organize the cytoskeleton accordingly (Huveneers & Danen, Journal of Cell Science, 122: 1059-1069, 2009).

Native collagen has a triple helical structure and forms microfibrils. A microfibril is composed of many tropocollagen helices, and each of these is assembled from three polypeptide chains twisted together to form the triple helical, native structure composed of amino acids. At certain locations within each of the three polypeptide chains, there are specific repeated amino acid sequences of arginine-glycine-aspartate (RGD, where R is arginine, G is glycine, and D is aspartate).

Triple helical type I collagen contains two RGD moieties in each of its two α1 chains and 4 RGD units in its α2 chain for total of 8 RGD motifs. The RGD sequences are twisted within the triple helix structure of native collagen and are thus not readily exposed on the surface of triple helical native collagen molecules. The RGD sequences are thus hidden or "cryptic" within the native structure of collagen and not readily contacted by cells exposed to triple helical collagen in its native or non-denatured conformation. Thus, in the native form of collagen, cells such as fibroblasts, endothelial cells, platelets and stem cells, do not readily interact through the cells' αvβ3 integrins with the RGD tripeptide motifs. As well, flow-cytometric phenotyping and immunofluorescence phenotyping show that αv, αvβ3 and αvβ5 are expressed in all mononuclear cells (muscle precursors and interstitial cells) seeded on extracellular molecules such as gelatin, vitronectin and fibronectin (Sinanan et al. 2008, αvβ3 and αvβ5 integrins and their role in muscle precursor cell, adhesion. Biol. Cell. 100, 465-477).

Integrin binding RGD sites have been identified in collagen and many other ECM proteins, including vitronectin, fibrinogen, von Willebrand factor, collagen, laminin, osteopontin, tenascin and bone sialoprotein, as well as in membrane proteins. Certain integrins have been shown to bind to ECM molecules in a RGD dependent manner: α3β1; α5β1; α8β1; αIIβ3; αvβ1; αvβ3; αvβ5; αvβ6; αvβ8; and to some extent α2β1 and α4β1 (Hersel et al. Biomaterials 24:4385-4415, 2003). A predominant role of the RGD site is for endothelial adhesion and for binding of αvβ3 and αvβ5 integrins (Pedchenko et al. 2004, αvβ3 and αvβ5 integrins bind both the proximal RGD site and non-RGD motifs within noncollagenous (NC1) domain of the α3 chain of type IV collagen: implication for the mechanism of endothelia cell adhesion. J Biol Chem., 23: 279). Not surprisingly, since RGD motifs were found to promote cell adhesion and influence cell survival and cell metabolism, numerous polymers have been chemically functionalized with RGD peptides, including collagen for biomedical applications, including but not limited to tissue regeneration (Niu et al. J. Mater. Sci Technol. 21: 571-576, 2005; Hersel et al. 2003).

Damage or trauma to collagen, such as thermal injury or proteolytic attack in vivo by gelatinase enzymes, leads to the unwinding of native or triple-helical collagen. The scission and subsequent unwinding, also known as "denaturation" of native collagen renders it susceptible to further degradation and fragmentation into various peptides by proteases (eg, elastase, collagenases, gelatinases secreted by neutrophils, macrophages, fibroblasts, and keratinocytes, and stem cells) and more specifically by MMP2 and MMP9 gelatinases. Denatured collagen (also known as gelatin) and degraded collagen molecules leads to exposure of the RGD sequences that become biologically active and influence biochemical and cell interactions at these RGD-binding sites. Native collagen is generally remodeled in the body by collagenases and gelatinases that serve to expose the RGD moieties with resultant biological activity toward competent cells, including platelets, fibroblasts, keratinocytes, and stem cells. Other cells may interact with RGD, through integrin-mediated contact.

Cells bind to collagen using the α1β1, α10β1, α11β1, and α2β1 integrin receptors that are not "cryptic" or hidden within the helical structure of native type 1 collagen. On the other hand, partial or total denaturation of collagen type 1, reveals cryptic RGD motifs that are recognized by αvβ3, αvβ1 and α5β1 receptors as well as the αIIB β3 integrins on platelets. Therefore, cells show different biological activities, or may remain quiescent, depending on whether or not, their surface integrins contact and bind with, either native collagen or denatured collagen as each of these collagens will have distinct amounts and differing locations of unexposed and exposed bioactive amino acid sequences. For example, fibroblasts produce collagen for secretion and ECM remodelling, and assist in wound healing, bind the RGD sequence with αvβ3 integrins.

In industry, denatured collagen, is derived from native collagen in the presence of extreme heat, acid and base treatments that result in loss of the triple helical structure of collagen and degradation and hydrolysis of the polypeptide chains of collagen. Generally, the loss of the triple helical configuration (denaturing) of collagen is considered an adverse reaction to be avoided when purifying native collagen for biomedical applications such as tissue regeneration.

Wound healing requires angiogenesis, and revascularization or new blood vessel formation, and involves the processes of adhesion, invasion, migration, proliferation, and capillary tube formation by specific cells. New blood vessels grow from endothelial cells. Angiogenesis requires specific molecular interactions between vascular cells and components of the ECM. Microvascular endothelial cell surface receptors that are specific for the fibrin-rich provisional ECM are believed to be involved in angiogenesis. There are several integrin receptors, but only αvβ3 can recognize and bind all the provisional matrix proteins, including fibrin and fibronectin.

Because of the bioactivity of the RGD sequence and certain synthesized mimics of RGD, there have been attempts directed to introducing RGD moieties within materials to be used in tissue engineered products. For example, chemical coupling of synthetic amino acid moieties, RGD moieties, cyclic RGD agents as well as other compounds has been practiced. However, such covalent coupling reactions are difficult to control on large proteins and are generally not conducive to modifying integrated collagen materials.

U.S. Pat. No. 7,671,016 discloses RGD-enriched gelatins in which the RGD-enriched gelatin is prepared by recombinant DNA technology. U.S. 2010/0184183 discloses various physical treatments for stabilizing a collagen artificial matrix for tissue engineering procedures after or prior to associating with adhesion peptides such as RGD.

DHT (dehydrothermal treatment) is a technique for stabilising collagen and collagen composite materials. It is a physical treatment that involves subjecting collagen to increased temperature (>90° C.) while under vacuum. The process removes water from the collagen molecules, resulting in the formation of intermolecular crosslinks through condensation reactions either by esterification or amide formation. DHT treatment is preferred to other crosslinking methods as it does not involve the use of cytotoxic reagents, is simple and reliable. A further advantage of DHT treatment is the sterilisation provided by the high temperatures and exposure times used. Studies on DHT treatment have shown that increasing DHT temperature and exposure duration improves the mechanical properties of collagen fibres (Haugh, M. G. et al. Crosslinking and Mechanical Properties Significantly Influence Cell Attachment, Proliferation, and Migration, Within Collagen Glycosaminoglycan Scaffolds. Tissue Engineering, Part A, 2011).

Yannas et al. (*Phil. Trans. R. Soc. A* 2010 368, 2123-2139) teach that following freeze-drying, the highly porous collagen scaffold is cross-linked by a two-step process. The first step is a dehydrothermal treatment, which does not require use of a cross-linking agent. In this process, the scaffold is exposed to temperatures of 100° C. to 120° C., or as high as 180° C. under high vacuum. This step leads to dehydration of the scaffold to a level below about 2 wt %. Drastic dehydration is required for cross-linking of collagen by the formation of amide bonds between protein chains and probably also by the formation of collagen-chondroitin sulphate bonds, or collagen-carboxymethylcellulose bonds, if they are alone or in combination with collagen. Denaturation or gelatinization, or melting of the triple helical structure of collagen, occurs if the moisture content at the beginning of the heating process is high enough to induce melting of the triple helical structure at the dehydration temperature. In addition to the loss of specific ligands for cell binding, gelatin degrades in vivo at a very highly accelerated rate. Thus, Yannas and al. teach away from the use of DHT processed collagen as a wound covering, as it would suffer the "loss of specific ligands for binding, [and] gelatin degrades in vivo at a very accelerated rate."

In DHT crosslinking, a freeze-dried collagen matrix, sponge, foam, pad, etc. is exposed to one or both of heat and reduced pressure to cause initial dehydration followed by loss of additional water and formation of crosslinking bonds via an inter- or intra-molecular condensation process. DHT involves dehydrating the product to be crosslinked to a moisture content less than about 1%, and using sufficient additional heat or vacuum to achieve a desired crosslink density. At moisture contents well above 1% denaturation of the collagen triple helical content is expected as noted by Yannas et al., (2010). The high temperatures used during DHT crosslinking have been shown to denature collagen. Denaturation is defined as rearrangement of the triple helix into a random chain configuration. The temperatures used during DHT treatment break the hydrogen bonds that maintain the triple helical structure of collagen, altering it to a random coiled structure, especially when the moisture content is well above 1%. The destruction of the triple helical structure is a detriment as it reduces the differentiation of certain stem cells as noted by Liu, Y. et al. (One-Step Derivation of Mesenchymal Stem Cell (MSC)-Like Cells from Human Pluripotent Stem Cells on a Fibrillar Collagen Coating, Plos One, 2012, 7, e 33225). Thus, DHT crosslinking that induces denaturation of the collagen fibrillar structure is seen as undesirable for the preparation of suitable scaffolds for cellular seeding and cellular maintenance.

It is known that the chemical changes produced by DHT may also adversely affect the cells embedded in the scaffold. If not applied appropriately, DHT crosslinking is well known to change the chemical composition of collagen-based membranes. DHT crosslinking-induced changes in chemical composition could alter the cytocompatibility of the scaffold to accept stem cells and thus compromise the cellular attachment. Any cytotoxicity of strongly cross-linked, collagen-based materials could modify cell shape and significantly reduce cell growth. DHT crosslinking has also been postulated to significantly decrease the rate of cell migration by masking the integrin binding sites that promote cellular attachment. Furthermore, after crosslinking, fibroblasts adhered and proliferated on DHT scaffolds; however, cell metabolism was 12% less on DHT scaffolds (Haugh et al. 2011, The effect of dehydrothermal treatment on the mechanical and structural properties of collagen-GAG scaffolds, Royal College of Surgeons in Ireland e-publications@RCSI, 2009, 21 pp.) noted that collagen denaturation increased with both DHT exposure and temperature. Increasing exposure period had no effect on denaturation at 105° C. and 180° C. However, at 120° C. and 150° C. denaturation increased with exposure period. Scaffolds contained 25% denatured collagen after treatment at 105° C. for 24 h and 60% denatured collagen after extensive treatment at 180° C. for 120 h. Thus, DHT crosslinked collagen is known to reduce cell metabolism and mask integrins (Jason W. Drexler and Heather M. Powell. Dehydrothermal crosslinking of electrospun collagen. Tissue Engineering Part C: Methods, 2011, 17: 9-17.

U.S. Pat. No. 4,412,947 discloses the dehydrothermal manufacture of a collagen sponge using native collagen in substantially pure form. A collagen solution is frozen with a temperature reduction rate of about −18° to −24° C./hour so that the ice crystals formed are extremely small and do not sever the crosslinkages or collagen chains, thus retaining the nativity and natural insoluble characteristics of the particulate collagen.

U.S. Pat. No. 4,948,540 teaches a collagen sheet material using DHT processing that must allow the collagen to retain its native structure. U.S. Pat. No. 6,309,454 teaches that denaturation of collagen in freeze-dried collagen sponges is to be minimized and that in the freeze-dried collagen sponges the collagen is stabilized against denaturation by the gamma irradiation in the sterilizing cycle.

U.S. Pat. No. 7,393,437 teaches that the harsh processing conditions of DHT treatment denature the native collagen, and as a result, "a long-felt need has existed for alternative methods of enhancing the physico-chemical properties of collagen coupled with features such as rapid and efficient processing, nil toxic substances, non-thermal processing and absence of denaturation of collagen".

US2010/0256774 teaches the use of DHT treatment at temperatures ranging from 80° C.-120° C. to preserve the visible band of collagen, thus indicating that the native structure of collagen is maintained after DHT treatment. Native-form Type I collagen fibrils typically display a banding pattern with 67 nm spacing when visualized with electron microscopy.

U.S. 2004/0028738 teaches that DHT treatment of collagen causes fragmentation of collagen molecules, and is disadvantageous for the preparation or collagenous materials.

U.S. 2010/00184183 teaches "to use genipin associated, or not, with other physical treatments such as UV, beam ionizing radiation, dehydration and thermal treatment (dehydrothermal crosslinking (DHT) KS Weadock and al (1996) for stabilizing the collagen artificial matrix (collagen, gelatin or chitosan), for tissue engineering procedures after or prior to associating with adhesion peptides such as RGD". Thus exogenous RGD moieties are added, and covalently bound to the collagen material.

From the aforementioned, there appears to be a need to provide for collagen materials with RGD functionalities to be presented on the surface of collagen molecules for biomedical applications, in a way that maintains the biological distribution and density of the RGD motifs in collagen and rendering the RGD non-cryptic.

There is also a need to provide a safe method to make such desired collagen materials without use of toxic chemicals. The use of DHT to provide denatured collagen with exposed RGD for cell activation has not been previously desired nor presented.

SUMMARY OF THE INVENTION

The invention relates to biocompatible, bioactive collagen biomaterials that provide sufficient exposed RGD peptides for cell activation and also sufficient native collagen for physical support for a variety of applications in vivo and ex vivo.

The biocompatible, bioactive collagen biomaterial of the invention comprises a collagen source with sufficiently exposed RGD motifs to elicit cell activation and sufficient triple helix native collagen structure for physical characteristics such that the biomaterial can be used in a wide variety of applications. In aspects the biomaterial is solely native collagen but produced by a process that sufficiently exposes RGD motifs while maintaining a level of structural integrity of the collagen. In other aspects, the bioactive collagen biomaterial of the invention comprises native collagen and one or more of denatured collagen (gelatin) and hydrolyzed collagen—the later two having exposed RGD motifs that would be available for cellular interaction.

Thus in an embodiment of the invention, the bioactive collagen biomaterial comprises native collagen and one or more sources of non-cryptic RGD peptide. The native collagen provides structure for the biomaterial while the non-cryptic RGD peptide source provides for the activation of a variety of cells via integrin binding. The RGD peptide motif can bind integrins in the ECM and thus have effect on a variety of the ECM proteins such as vitronectin, fibrinogen, von Willebrand factor, collagen, laminin, osteopontin, tenascin and bone sialoprotein. Such binding is fortuitous for the influencing biochemical and cell interactions at the RGD binding sites to promote one or more of cell adhesion, influence cell survival, cell metabolism. Further, the source of RGD peptide(s) has a biodegradable/biosorbable property. Thus the bioactive collagen biomaterial of the invention has structural, bioactive and biodegradable/biosorbable properties and thus can be fabricated in a variety of formats and used in conjunction with other devices or structures. The bioactive collagen biomaterial of the invention is stable in vivo and in vitro.

The bioactive collagen biomaterial can be fabricated without cross-linking, by chemical cross-linking, by DHT treatment and combinations thereof.

It is an object of the present invention to provide a bioactive collagen biomaterial composition having cryptic RGD motifs that can be used as a starting material for the facile manufacture of a bioactive collagen biomaterial with resultant denatured collagen with exposed (non-cryptic) RGD peptides (i.e. motifs) to be used as tissue covering or wound dressing for chronic and hard-to-manage wounds, such as diabetes wounds, foot ulcers, leg ulcers, skin ulcers or bedsores noted in diabetics and elderly patients, and is one that promotes angiogenesis and wound closure by having a composite collagen material.

As manufactured as a wound dressing, the RGD peptides are exposed to wound fluids that contain cells (such as, fibroblasts, granulocytes, keratinocytes, endothelial cells) and ECM materials; the cells may be host-derived cells, or they may be autologous or allogenic stem cells previously added to the wound by injection, infusion or direct topical application. While not invoking any particular theory, it is disclosed that cells, including stem cells exposed to denatured collagen in a crosslinked collagen composite material of this invention elicit an accelerated wound healing cascade, by contact with exposed RGD peptides presented (in aspects by DHT treatment), in vivo to be used in humans, and in veterinary applications, namely equine, canine and feline, and other mammalian species to induce tissue regeneration of wounds.

In accordance with one aspect of the present invention the collagen for use in the invention is a Type 1 fibrillar native porcine or bovine collagen matrix in which the RGD moieties are cryptic. The biomaterial is made as a starting composition in the form of a slurry/suspension/colloid with solvent and is frozen/lyophilized such that it does not contain substantial amounts of solvent and comprises native collagen, or a mixture of native collagen, and biocompatible polymers, including denatured collagen, and optional therapeutic compounds; EDTA may be added as a preservative.

In accordance with further aspects of the present invention is a Type 1 fibrillar native bioactive collagen biomaterial in which the RGD moieties are cryptic and blended with Type 1 denatured collagen to form a composition. The biomaterial composition is frozen/lyophilized such that it does not contain substantial amounts of solvent and comprises native collagen or a mixture of native and denatured collagen, biocompatible polymers, and optional therapeutics and is crosslinked using chemical or a dehydrothermal cross linking method. In desired embodiments, DHT treatment exposes the native collagen to high temperatures sufficient to cause denaturing of the native collagen with subsequent and beneficial exposure of RGD motifs, previously cryptic in the native collagen, while crosslinking the collagen stabilizes the collagen composite structure. This method provides a facile method to render a native Type 1 collagen matrix into its denatured form while simultaneously providing non-cryptic RGD in a rapid and simple method that obviates the need for chemical-induced addition of RGD or RGD-mimetic peptides and reduces expense.

In accordance with another aspect of the present invention is a lyophilized denatured bioactive collagen biomaterial having non-cryptic RGD moieties exposed in varying amounts. The biomaterial may be cross linked or not. By its very nature, the timing of the DHT process can provide various amounts of denatured collagen simply by increasing the length of time the collagen is exposed to DHT processing.

In aspects, native collagen and denatured collagen are used as the protein components of the matrix. In alternative aspects, collagen and denatured collagen, denatured according to specific denaturation parameters intrinsic to the DHT process well-known to those experienced in the art, are used in combination, on the collagen composite matrix.

In accordance with another aspect of the present invention is a bioactive collagen biomaterial comprising; a mixture of protein comprising native collagen and denatured collagen and biocompatible polymers, wherein RGD motifs are non-cryptic. In aspects, the mixture may further comprise one or more polymers each of carboxymethylcellulose, hyaluronic acid, chondroitin sulphate, alginate, chitosan, and said mixture is lyophilized and crosslinked using DHT processing.

In aspects of the invention, one or more of a pharmaceutical, chemical or other agent may be added before freeze-drying and DHT cross-linking reaction.

According to an aspect of the present invention is a bioactive collagen biomaterial that provides sufficiently non-cryptic RGD motifs and sufficient triple helix structure for physical support for applications in vivo and ex vivo. In aspects, the biomaterial is lyophilized and optionally cross-linked and optionally comprises therapeutic agents.

According to an aspect of the present invention is a bioactive collagen biomaterial comprising native collagen and one or more sources of non-cryptic RGD peptide, wherein said biomaterial is lyophilized and cross-linked with sufficient non-cryptic RGD peptide exposed to evoke cellular activation when in contact with a wound.

According to an aspect of the present invention is a bioactive collagen biomaterial composition comprising native collagen, one or more sources of non-cryptic RGD peptide and solvent.

According to a further aspect of the present invention, is a lyophilized bioactive collagen biomaterial comprising native collagen and one or more sources of non-cryptic RGD peptide.

According to a further aspect of the present invention is a lyophilized flexible, biosorbable and bioactive collagen biomaterial comprising native collagen and one or more sources of non-cryptic RGD peptide.

According to a further aspect of the invention is a bioactive collagen biomaterial composition comprising native collagen and one or more sources of non-cryptic RGD peptide, where the source of non-cryptic RGD peptide is denatured collagen and/or hydrolyzed collagen.

According to a further aspect of the invention is a bioactive collagen biomaterial comprising native collagen and one or more sources of non-cryptic RGD peptide, where the source of non-cryptic RGD peptide is denatured collagen and/or hydrolyzed collagen.

In any aspect of the invention the native collagen can be fibrillar type 1 collagen.

In aspects, the biomaterial is absent of any chemical modification.

According to an aspect of the invention is a bioactive collagen biomaterial composition comprising;
  native collagen;
  denatured collagen;
  solvent; and
  optionally hydrolyzed collagen, wherein the denatured collagen and hydrolyzed collagen contain non-cryptic RGD peptides.

According to another aspect of the invention is a lyophilized bioactive collagen biomaterial comprising;
  native collagen;
  denatured collagen;
  optional cross-linking agent; and
  optionally hydrolyzed collagen, wherein the denatured collagen and hydrolyzed collagen contain non-cryptic RGD peptides.

According to an aspect of the invention is a bioactive collagen biomaterial composition comprising;
  native collagen;
  denatured collagen;
  solvent;
  optionally hydrolyzed collagen;
  optional chemical agents;
  optional biological polymers; and
  optional plasticizers,
  wherein the denatured collagen and hydrolyzed collagen contain non-cryptic RGD peptides.

According to an aspect of the invention is a lyophilized bioactive collagen biomaterial comprising;
  native collagen;
  denatured collagen;
  optionally hydrolyzed collagen;
  optional chemical agents; and
  optional biological polymers,
  wherein the denatured collagen and hydrolyzed collagen contain non-cryptic RGD peptides.

The invention also encompasses method for making the bioactive collagen biomaterial and biomaterial composition of the invention.

According to an aspect of the invention is a method for making a bioactive collagen biomaterial composition, the method comprising admixing;
  native collagen;
  denatured collagen;
  solvent;
  optional hydrolyzed collagen;
  optional cross-linking agent;
  optional chemical agents; and
  optional biological polymers, wherein the denatured collagen and hydrolyzed collagen contain non-cryptic RGD peptides.

According to an aspect of the invention is a method for making a bioactive collagen biomaterial, the method comprising;
(i) admixing;
native collagen;
denatured collagen;
solvent;
optional hydrolyzed collagen;
optional cross-linking agent;
optional chemical agents; and
optional biological polymers,
wherein the denatured collagen and hydrolyzed collagen contain non-cryptic RGD peptides,
(ii) freezing and lyophilizing (i) to remove solvent.

According to an aspect of the invention is a method for making a bioactive collagen biomaterial, the method comprising;
(i) admixing;
native collagen;
denatured collagen;
solvent;
optional hydrolyzed collagen;
optional chemical agents; and
optional biological polymers,
wherein the denatured collagen and hydrolyzed collagen contain non-cryptic RGD peptides,
(ii) freezing and lyophilizing (i) to have a moisture content of about 2% or more and cross-linking by dehydrothermal crosslinking.

According to another aspect of the invention is a method for making a bioactive collagen biomaterial, the method comprising;
(i) admixing;
native type 1 collagen;
denatured and/or hydrolyzed collagen having exposed RGD sequences;
solvent;
PHMB and/or EDTA;
optional chemical agents; and
optional biological polymers,
(ii) freezing and lyophilizing (i) to have a moisture content of at least about 1% by wgt or more and cross-linking by dehydrothermal crosslinking. In aspects, the moisture content is reduced to any integer in the range of about 2-15% or more, including ranges therein between. Such moisture content when applying the DHT results in the exposure of RGD in the native collagen.

According to another aspect of the invention is a method for making a bioactive collagen biomaterial, the method comprising;
(i) admixing;
native type 1 collagen;
solvent;
PHMB and/or EDTA;
optional chemical agents; and
optional biological polymers,
(ii) freezing and lyophilizing (i) to have a moisture content of about 1% to 15% and cross-linking by dehydrothermal crosslinking.

According to a further aspect of the invention is a method for the treatment of a wound, the method comprising applying a bioactive collagen biomaterial to said wound, wherein said biomaterial comprises native collagen and one or more sources of non-cryptic RGD peptide, wherein said biomaterial is lyophilized and cross-linked with sufficient non-cryptic RGD peptide exposed to evoke cellular activation.

According to a further aspect of the invention is a tissue covering or wound dressing comprising a biocompatible, bioactive collagen biomaterial, comprising native collagen and one or more sources of non-cryptic RGD peptide.

According to a further aspect of the present invention is a lyophilized flexible, porous, cross linked biosorbable wound dressing comprising a bioactive collagen biomaterial comprising native collagen and one or more sources of non-cryptic RGD peptide.

In further aspects are:
A lyophilized bioactive collagen biomaterial comprising;
native collagen;
denatured collagen;
optionally a cross-linking agent;
optionally hydrolyzed collagen,
optionally a chemical agent;
optionally biological polymers; and
optional plasticizers,
wherein one or more of the native collagen, denatured collagen and hydrolyzed collagen contain non-cryptic RGD motifs that bind receptors in cells, tissues and/or organs when said biomaterial is in contact with said cells, tissue and/or organs to effect cell activation and wound repair.

A porous, flexible, biocompatible lyophilized bioactive collagen biomaterial comprising;
native collagen;
denatured collagen;
optionally hydrolyzed collagen;
PHMB;
EDTA;
optional pharmaceutical agents; and
optional biological polymers,
wherein the denatured collagen and hydrolyzed collagen contain non-cryptic RGD peptides.

A method for making a bioactive collagen biomaterial, the method comprising;
(i) admixing;
native collagen;
optional denatured collagen;
solvent;
optional hydrolyzed collagen;
optional cross-linking agent;
optional chemical agents; and
optional biological polymers,
(ii) forming a slurry of (i);
(iii) lyophilizing (ii);
(iv) subjecting (iii) to DHT for a time, temperature and pressure to effectively denature the native collagen to expose sufficient RGD motifs for cellular interaction while maintaining sufficient structural integrity to the native collagen.

A method for making a bioactive collagen biomaterial, the method comprising;
(i) admixing;
native collagen;
optional denatured collagen;
solvent;
optional hydrolyzed collagen;
PMHB and EDTA; and
optional biological polymers,
wherein the denatured collagen and hydrolyzed collagen contain non-cryptic RGD peptides,
(ii) freezing and lyophilizing (i) to have a moisture content of about 2% or more and cross-linking by dehydrothermal crosslinking.

According to an aspect of the invention is the use of DHT for the activation of native collagen in a lyophilized collagen matrix, wherein said activation comprises the exposure of RGD motifs and maintaining collagen structure.

A bioactive collagen biomaterial comprising sufficiently exposed RGD motifs for cell activation and sufficient triple helix native collagen structure for physical integrity.

In aspects, is a method for the treatment of a wound, the method comprising applying the biomaterial as described herein to said wound, the sufficiently exposed RGD motifs evoking cellular activation.

In aspects is a tissue covering comprising the biomaterial as described herein.

In aspects is a wound covering comprising the biomaterial as described therein.

In aspects when applied to an open wound, the covering acts as a cover that impedes microbial contamination, absorbs wound exudate, and functions as depot for cells within the wound bed activating essential biochemical factors, including enzymes, hormones, amino acids, cell signal molecules, such as RGD, ECM molecules, and cells that promote biological activation effects, such cell migration, remodelling of the ECM, angiogenesis, and wound closure.

DETAILED DESCRIPTION OF THE INVENTION

The invention provides a novel bioactive collagen biomaterial that has sufficiently exposed RGD (i.e. non-cryptic RGD tripeptide motifs) that provides for cellular interaction in vivo and ex vivo, thus having a variety of uses in medical and scientific applications. The RGD motifs are sufficiently exposed in the material and thus can be available to cellular integrins to evoke a cellular response and may further promote physiological functions such as wound repair, cell adhesion, wound closure, angiogenesis and the like.

The bioactive collagen biomaterial is made initially from a composition that comprises a solvent, collagen source with cryptic and/or non-cryptic RGD motifs, optional agents such as plasticizers, chelators, antiseptics, antimicrobials, peptides, growth factors, steroids, cells and the like and combinations thereof. This forms a colloid/slurry/mixture/suspension (any of these terms may apply) that is lyophilized (freeze-dried) and further that moisture levels are reduced and forms a bioactive collagen biomaterial that is porous that can be configured into any shape and thickness depending on the end use. This biomaterial can be further cross-linked if desired by chemical cross linking means or by DHT, or both. Alternatively, the formed bioactive collagen biomaterial can be soaked or dipped into a solution that comprises the agent for which is desired to be delivered to a tissue, organ or cell(s). In other aspects, the agent can be initially provided and lyophilized into the biomaterial and further dipped into a solution of desired agent. Thus the bioactive collagen biomaterial of the invention can be "loaded" with any desired agent before and/or after lyophilisation.

The bioactive collagen biomaterial is biocompatible, bioresorbable and can be flexible. As lyophilized it is a porous structure suitable for the incorporation of a variety of agents and/or biological polymers. Pore sizes can be from 0.1 µm to about 500 µm and any integer and range therein between. It can be made into a variety of formats, a variety of shapes, a variety of thicknesses, fixed to a variety of surfaces. It can also be admixed with or dispersed within a variety of other materials. The bioactive collagen biomaterial is therefore suitable for several types of scientific and medical applications.

The biomaterial of the invention can be made into a variety of formats such as pads, scaffolds, films, tissue coverings, surgical implants, dental implants, bone coverings, topical would dressings, tissue barriers, organ barrier, sponges and the like. The biomaterial of the invention can be fixed to surfaces such as metals, synthetic polymers such as silicone and ceramics such as ceramic implants. The biomaterial of the invention can be admixed with adhesive films of wound dressings such as acrylate adhesives and silicone adhesives.

In other aspects of the present invention, the biomaterial may be provided as an occlusive device comprising an occlusive structure and the collagen matrix, wherein the biomaterial has opposing surfaces such that one surface of the biomaterial is affixed to one surface of the occlusive structure, that is gas and liquid permeable, with the other surface of the matrix being adapted to cover and be in contact with tissue. In such aspects the occlusive device may be a polymer film that is gas and liquid permeable or may be fitted with pores or holes or slits to make it gas and liquid permeable.

The bioactive collagen biomaterial of the invention can also be fabricated as a device in conjunction with other materials such as, but not limited to metals useful as dental and orthopaedic implants, polymer sheets, films, threads, membranes or meshes of silicone, polyurethane, polyethylene, polymeric fibers, nylon, silk, cellulose and combinations thereof. The fabrication may be carried out by chemically modifying the surface of the other material by methods of chemical modification, gamma-irradiation, plasma or corona discharge and/or by UV light so that reactive groups are introduced onto the surface of the material.

Briefly, the bioactive collagen biomaterial of the invention is made from a bioactive collagen biomaterial composition (in the form of solution or slurry/suspension/colloid/dispersion), that comprises native collagen, and/or denatured collagen, and/or hydrolyzed collagen and a solvent. This composition is then lyophilized (freeze dried) under suitable pressures and temperatures to provide a lyophilized bioactive biomaterial composition that may be further cross-linked. Suitable pressures are about $10^{-5}$ mm or more.

The bioactive collagen biomaterial comprises native collagen and a source of RGD peptide that is non-cryptic. Any of the collagens for use in the biomaterial can be from any human and/or animal source. Bovine and porcine sources are used in aspects. It can be fabricated or purchased from a commercial source. The source of RGD peptide can be from denatured collagen and from hydrolyzed collagen. Indeed, depending on the nature of the method of fabrication, the native collagen can also have some RGD motifs exposed when DHT is utilized to manufacture the biomaterial. The native collagen may be type 1 collagen which also serves to increase the mechanical stability of the biomaterial and to reduce its rate of resorption by the body In aspects of the invention Type 1 collagen is denatured using any method well-known method. For example, collagen is denatured by exposure to heating at 100° C. in aqueous solution for various periods of time. Type 1 collagen may also be denatured by boiling in 0.02 M acetic acid or other appropriate method. Alternatively, native or denatured or hydrolyzed Type 1 collagen may be purchased from an appropriate manufacturer as is known.

In aspects of the invention solutions of native and denatured and/or hydrolyzed collagens are admixed in various amounts to produce a collagen composition comprising any combination of native collagen and denatured and hydrolyzed collagen. In aspects of the invention the collagen matrix may be all native collagen. In aspects of the invention the collagen matrix may be all denatured collagen. In aspects of the invention the collagen matrix may be all hydrolyzed collagen.

In the aspect of the invention where the collagen matrix may be all native collagen, it is denatured during the lyophilisation procedure by raising the temperature by an appropriate amount to effect denaturation of the native collagen thus exposing RGD motifs. This can be effected by using the DHT processing technique. DHT is effected to provide the desired amount of RGD exposure while still maintaining some of the triple helix structure for stability. The reduced pressure and temperature is effected to provide moisture content of about above 1% for a time, temperature and pressure to cause the desired denaturation and cross-linking. This has not been previously realized in a manner to produce a biomaterial that is bioactive and useful for wound repair, cell adhesion, wound closure and and/or angiogenesis.

In aspects of the invention the preferred protein solution contains both native and denatured collagen such that the native collagen:denatured collagen:hydrolyzed collagen ratio is but not limited to ratios as follows: 1:0:0, 1:1:1, 1:2:1, 1:3:1, 1:4:1, 1:5:1, 5:1:0, 4:1:1, 3:1:1, 2:1:1, 0:2:1, 0:3:1, 0:4:1, and 0:5:0.

It is understood that any combination of the collagens can be used to practice the embodiments of the present invention. The total amount of collagen in the final biomaterial is at least 55% by weight. The ratios given serve only as guidelines and one should not be limited by any particular ratio.

Suitable solvents for use in making the bioactive collagen biomaterial composition are selected from the group consisting of water, methanol, ethanol, isopropanol, dimethylsulfide (DMS), and mixtures thereof. Solvents may be provided in any amount as is understood by one of skill in the art as the solvent will be evaporated in the final biomaterial. In aspects of the invention the solvent is water or if used in addition with a polar organic solvent, the solvent ratio is typically about 9:1, water to polar organic solvent, in the final mixture. The solution/suspension of native collagen, and/or denatured collagen, and/or hydrolyzed collagen are mixed with solvent and frozen and lyophilized.

Prior to the freezing and lyophilisation, suitable agents and/or biological polymers may be added. Alternatively, such agents and/or biological polymers may be provided after lyophilisation by dipping the biomaterial so formed into a suitable solution or soaking it therein. Such agents may be provided in desired amounts of about 0.001% up to about 5% or more by weight of the biomaterial.

Suitable chemical agents for incorporation into the biomaterial are metal chelators (such as for example EDTA), antiseptics, antimicrobials (for example PHMB), pharmaceuticals, cosmetic agents, peptides, growth factors, steroids, cells and combinations thereof.

More specifically, cosmetic agents may include active ingredients which are intended to be applied externally to humans for the purpose of cleansing, care or for influencing the appearance or body odour or for imparting odour impressions, unless they are intended primarily for alleviating or eliminating diseases, afflictions, physical injuries or pathological complaints. Within this context, the materials according to the invention for cosmetic use are, for example, skin washing and cleansing agents, skin care agents, in particular facial skin care agents, cosmetics for the eyes, lip care agents, nail care agents, foot care agents, depigmenting agents, deodorants, antihydrotics, or such agents in combination. Use as a cosmetic dressing or mask is also within the scope of the invention.

Dermatological, therapeutic activity includes: anti-acne agents, antimicrobial agents, antiperspirants, astringents, deodorants, depilatory agents, conditioning agents for the skin, skin-smoothing agents, agents for increasing skin hydration such as, for example, dexpanthenol (panthenol, pantothenol), glycerol or urea as well as other NMFs (natural moisturising factors) such as, for example, pyrrolidonecarboxylic acid, lactic acid and amino acids, sunscreens, keratolytics, radical acceptors for free radicals, antioxidants, antiseborrheics, anti-dandruff agents, antiseptic active ingredients, active ingredients for treating the signs of skin ageing and/or agents which modulate skin differentiation and/or proliferation and/or pigmentation, protease inhibitors, for example MMP (matrix metalloproteinase) inhibitors, glycation inhibitors for reducing the formation of AGE (advanced glycation end-product) substances, vitamins such as vitamin C (ascorbic acid) and its derivatives, such as, for example, glycosides such as ascorbyl glucoside, or esters of ascorbic acid such as sodium or magnesium ascorbyl phosphate or ascorbyl palmitate and stearate, L-ascorbic acid phosphate esters, alkali metal salts, such as sodium and potassium salts, of L-ascorbic acid phosphate esters; alkaline earth metal salts, such as magnesium and calcium salts, of L-ascorbic acid phosphate esters; trivalent metal salts, such as aluminium salts, of L-ascorbic acid phosphate esters; alkali metal salts of L-ascorbic acid sulfate esters, such as sodium and potassium salts of L-ascorbic acid sulfate esters; alkaline earth metal salts, such as magnesium and calcium salts, of L-ascorbic acid sulfate esters; trivalent metal salts, such as aluminium salts, of L-ascorbic acid sulfate esters; alkali metal salts, such as sodium and potassium salts, of L-ascorbic acid esters; alkaline earth metal salts, such as magnesium and calcium salts, of L-ascorbic acid esters; and trivalent metal salts, such as aluminium salts, of L-ascorbic acid esters, any natural, nature-identical and artificial peptides such as, for example, neuropeptides, antimicrobial peptides and matrikines with and without modification by covalent bonding to a fatty acid or esterification.

Agents having an irritant side-effect, such as alpha-hydroxy acids, β-hydroxy acids, α-keto acids, β-keto acids, retinoids (retinol, retinal, retinic acid), anthralins (dioxyanthranol), anthranoids, peroxides (benzoyl peroxide), minoxidil, lithium salts, antimetabolites, vitamin D and its derivatives; catechols, flavonoids, ceramides, polyunsaturated fatty acids, and essential fatty acids.

Pharmaceutical agents (medicaments) are those which, within the meaning of pharmaceutical law, are intended inter alia for healing, alleviating or preventing diseases, ailments, physical injuries or pathological complaints. Suitable according to the invention are in particular those agents and active ingredients which are intended for external or transdermal application, in particular in the field of wound treatment and healing and in the field of the treatment of burns, in particular for first aid for burns.

Agents for dermal or transdermal application are in particular skin-active but also transdermal active ingredients. They include, for example: agents for the treatment of burns, agents for the treatment of skin diseases, analgesics for external application, for example dextropropoxyphen, pentazocine, pethidine, buprenorphine; antirheumatics/antiphlogistics (anti-inflammatories) (NSARs), for example frankincense or frankincense extract, indometacin, diclofenac, naproxen, ketoprofen, ibuprofen, flurbiprofen, salicylic acid and derivatives thereof, such as acetylsalicylic acid, oxicams; steroid hormones, for example corticoids and glucocorticoids such as hydrocortisone, cortisol, cortisone acetate, cloprednol, prednisone, prednisolone, deflazacort, fluocortolone, triamcinolone, betamethasone, betamethasone valerate, mometasone furoate, dexamethasone, methylprednisolone, ethynyloestradiol, medroergotamine, dihydroergotoxine; antigout agents, for example benzbromarone, allopurinol; external dermatic agents, antihistamines such as brompheniramine, bamipine; antibiotics such as erythromycin, clindamycin, tetracycline, including antibacterial agents such as, for example, colloidal silver and silver salts such as silver chloride, silver nitrate, silver iodide or further silver-containing wound treatment agents known from the prior art; antimycotics, peptide medicaments, antiviral active ingredients, anti-inflammatory active ingredients, antipruritic active ingredients such as anaesthetising active ingredients, for example antihistamines, benzocain, polidocanol or corticoids and glucocorticoids; anti-acne agents; antiparasitic active ingredients; hormones for external application; vein therapeutics; immune suppressants such as calcineurin inhibitors such as tacrolimus and pimecrolimus, mineral substances and trace elements, such as, for example, inorganic or organic selenium compounds, zinc and zinc salts, etc., all for dermal or transdermal application.

Agents may be selected from the group of the skin-like lipids, comprising, for example, phospholipids, neutral lipids and sphingolipids as well as components of the natural moisturising factor (NMF) of the skin, comprising, for example, urea, amino acids and carboxylic acids, pyrrolidonecarboxylic acid, sodium, potassium, calcium, magnesium, lactate (lactic acid), citrate, chloride, phosphate, etc., uric acid and other organic acids.

Particular preference is further given to those active ingredients which are used in the field of wound treatment, in particular for the treatment of chronic wounds, decubitus, Ulcus cruris, diabetic foot syndrome, etc., such as, for example, analgesics, for example immune suppressants, hormones, anaesthetising active ingredients, antiparasitic, fungicidal or antimycotic and antibacterial active ingredients such as in particular silver-containing active ingredients such as, for example, silver nitrate, silver chloride, silver iodide, micro-sized silver particles or further silver-containing wound treatment substances known from the prior art, active ingredients for supporting and regulating the wound environment such as in particular electrolytes, silica, mineral substances and trace elements such as, for example, potassium, magnesium, calcium, selenium, iodine, etc., active ingredients for achieving a wound debridement such as, for example, collagenases or other suitable proteolytic enzymes known in the prior art, as well as active ingredients for assisting wound healing such as, for example, growth factors, enzyme inhibitors, matrix proteins or extracellular matrix constituents or soluble (low molecular weight) protein and peptide constituents, collagen types other than the type I, III and V collagens already contained in the collagen suspension used according to the invention.

Particularly useful agents from the field of the wound treatment agents are selected from silver-containing active ingredients such as in particular silver nitrate, silver chloride, micro-sized silver particles, tacrolimus, pimecrolimus, antihistamines, polidocanol, frankincense/frankincense extract, capsaicin, tannin, St. John's Wort oil/St. John's Wort extract, evening primrose oil, dexpanthenol as well as inorganic or organic selenium compounds, zinc and zinc salts.

Further useful agents are those from the group of the proteinogenic active ingredients, preferably comprising growth factors, proteinogenic hormones, enzymes, coenzymes, glycoproteins, blood clotting factors, other cytokines and variants of the above-mentioned active ingredients prepared by recombinant techniques.

Growth factors which can be used according to the invention are selected from the group consisting of VEGF (vascular endothelial growth factor), bFGF (basic fibroblast growth factor), FGF-1 (acid fibroblast growth factor), TGF-$\beta$, TGF-$\alpha$ (transforming growth factor $\beta$ or $\alpha$), EGF (endothelial growth factor), HGF (hepatocyte growth factor), TNF$\alpha$ (tumor necrosis factor $\alpha$), IGF I and II (insulin-like growth factor/insulin binding growth factor I and II), heparin binding growth factor I and II, PDGF (platelet derived growth factor), PD-ECGF (platelet derived endothelial cell growth factor), BMP (bone morphogenetic growth factor), GHRP (growth hormone release factor), cartilage inducing factor A and B, bone growth factors, interleukin 8, angiopoietin, angiogenin, aprotinin, and vWF (von Willebrand factor).

Glycoproteins as active ingredients include, for example, immunoglobulins and antibodies. Other cytokines as active ingredients include, for example, interleukins and interferon. Further active ingredients are those which have a haemostatic action, such as blood clotting factors such as, for example, thrombin, fibrinogen or cholesteryl sulfate (e.g. sodium cholesteryl sulfate), or active ingredients having an activating action on factors and substances of the extrinsic and/or intrinsic clotting cascade, such as, for example, phospholipids, kaolin, aprotinin, concentrates of factor or factors, tissue factor or calcium ions. The collagen material per se can also have certain therapeutic actions, such as in particular a haemostatic action or a positive assisting effect in wound healing. It is, however, not an active ingredient within the meaning of the invention.

The above-mentioned agents may be added and are present in the cross linked collagen biomaterial on their own or in a combination of a plurality of active ingredients, in aspects in an amount of advantageously up to 40 wt. %, or up to 60 wt. %, or up to 80 wt. %, based on the freeze-dried end product. In one aspect, the pharmaceutical, chemical and/or other agent can be incorporated in an amount of about 0.001 to 0.01%, 0.01% to about 1.0% or 1.0%-10% into the initial formulation step or about 0.001% to about 25% after lyophilization. In another aspect the lyophilized matrix can be soaked in a solution of the desired pharmaceutical, chemical and/or other agent and then the matrix may be used after soaking or may be re-lyophilized.

In an embodiment of the invention involving wound treatment for example, the bioactive collagen biomaterial of the invention may comprise polyhexamethylene biguanide (PHMB) N-(3-aminopropyl)-imidodicarbonimidic diamide, or also known also known as polyhexanide Poly(hexamethylenebiguanide) hydrochloride), Poly(iminocarbonimidoyliminocarbonimidoylimino-1,6-hexanediyl) hydrochloride, Poly(iminoimidocarbonyl-iminoimidocarbonyl-iminohexamethylene) hydrochloride, Poly(iminoimidocarbonyliminoimidocarbonyliminohexamethylene) hydrochloride, with the following trade names, Baquacil, Caswell No. 676, Cosmocil CQ, EPA Pesticide Chemical Code 111801, Polihexanido, Polihexanidum, PP 073 and UNII-322U039G as an antiseptic agent to deter colonization of the collagen biomaterial while protecting the surface of the skin or wound from microbial contamination, or reducing the microbial flora within the wound. The PHMB may be added in an amount of about 0.001 to 0.01%, 0.01% to about 1.0%, or 0.05%-5%, or 0.1%-5% or 0.1%-0.3% of the biomaterial.

The biomaterial of the invention may further comprise ethylenediamine tetraacetic acid (EDTA), a metal chelator alone or in combination with the PHMB as a preservative agent added in an amount of about 0.001 to 0.01%, 0.01% to about 1.0%, or 0.05%-5%, or 0.1%-5%, or 0.1%-0.3% of the biomaterial.

In embodiments for example for wounds, the agents for use in conjunction with the present invention include but are not limited to cells, stem cells, angiogenic factors such VEGF, platelet derived growth factors, growth hormones, antiseptics, polyhexamethylbiguanide gluconate, chlorohexidine gluconate, triclosan, povidone-iodine, silver lactate or agents such as antibiotics immunosuppressants, antiproliferative agents, anti-inflammatory agents, antivirals, cells and combinations thereof.

The selection of the agent for use with the matrix of the invention will depend on its end use. For example, if used for the treatment of diabetes-related skin ulcer conditions, an antiseptic agent, preferably PHMB and at least EDTA may be provided to the matrix before and/or after lyophilisation; or an angiogenic factor like human growth hormones or platelet derived growth factors, or platelet derived lysate may be added to the matrix before or after lyophilization.

In further aspects of the invention polymers and other proteins may be added. Biocompatible polymers can be incorporated into the biomaterial. Suitable polymers for use may be selected from the group consisting of chitosan, cellulose, hyaluronic acid, chondroitin sulphate, carboxymethylcellulose and mixtures thereof.

Optional plasticizers can be added to the composition of the invention and are selected from glycerol, polyethylene glycol and sorbitol and provided in the non-crosslinked phase of the biomaterial, in a range of about 1-20 weight % of the total weight of the material, or from about 5-10 weight %, or in the range of about 1-5 weight %. The amount present in the final lyophilzed product is the same proportional amount once the solvent is removed.

In aspects structure forming proteins may be added such as matrix proteins, extracellular matrix constituents or soluble (low molecular weight) protein and peptide constituents, preferably from the group comprising elastin, elastin hydrolysates, glycosaminoglycans, such as heparan sulfate, chondroitin sulfate, dermatan sulfate, keratan sulfate, heparin and hyaluronic acid, proteoglycans, such as aggrecan, fibromodulin, decorin, biglycan, versican, perlecan, high-density basal membrane proteoglycan, syndecan and serglycine, fibrin, fibronectin, glucans, such as paramylon, etc. Most particularly preferred extracellular matrix constituents and structure-forming agents of that type are elastin and elastin hydrolysates, hyaluronic acid and fibronectin.

In the freeze-dried biomaterial such proteins can account in total for up to about 10 wt %, or up to 20 wt %, based on the dry mass of the freeze-dried end product.

For use in wound therapy, exposing cells to collagen and more specifically, specially configured collagen materials having denatured collagen, in the form of pads, sponges, foams, granules, hydrogels, slurries and the like as tissue or wound coverings would expose the non-advancing wound edge to the RGD amino acid sequence and help promote and accelerate wound closure. Similarly, by exposing stem cells to the RGD sequences in denatured collagen pads, sponges, foams, granules, hydrogels, slurries and the like would engage the cells' $\alpha v \beta 3$ integrins, and activate cells. Thus by placing stem cells into a wound bed and subsequently covering the wound bed with DHT-prepared collagen material, it is expected that accelerated wound healing would occur. As well, it is expected, that resident cells within the wound bed, such as, fibroblasts, platelets, keratinocytes, endothelial cells, granulocytes, etc. would contact the DHT-treated collagen and become activated through contact of their integrins with their ligands within the denatured collagen. While not ascribing to any particular theory of set of theories, cells, including stem cells exposed to the RGD sequence are biochemically activated to better promote tissue regeneration, angiogenesis, collagen deposition by fibroblasts, and wound closure by fibroblasts and other cells.

The present invention relates further to the bioactive collagen biomaterial according to the invention for use in at least one indication or application selected from the following group, which consists of: treatment of acute or chronic wounds, improvement of wound healing, equalising tissue defects, lining deep skin defects while building volume, assisting tissue regeneration, regeneration of the dermis, treatment of burns, use in plastic surgery, use after scar excision, combination therapy with autologous split-skin transplants, assisting the formation of granulation tissue, assisting angiogenesis, ensuring better scar quality, treatment of chronic wounds such as Ulcus cruris, decubitus and diabetic foot, treatment of open wounds, treatment of wound healing disorders, treatment of diseases with deep skin defects, production of a jaw implant, production of a bone implant, production of a cartilage implant, production of a tissue implant, production of a skin implant, production of a medical dressing, production of a transdermal dressing, production of a wound plaster, production of a wound bandaging material, production of a wound dressing and production of a cell culture matrix for cell multiplication for the implantation of cell matrix units, and in biotechnology in the production of model systems for the in vitro reproduction of tissue systems (e.g. skin model) for basic research, diagnostics and analysis.

Furthermore, the biomaterial according to the invention can also be used in vacuum-assisted wound treatment therapy, as is known in principle from the prior art and as described, for example, in US 2007/0027414 (the disclosure of which is herein incorporated by reference in its entirety). Because the biomaterial according to the invention can be flexible it can successfully be introduced into the wound bed in such a vacuum treatment, where they positively assist the removal of excess wound fluids owing to their good absorption and hydration properties. Transport of the exudate is already achieved on the one hand by the permeable, porous collagen matrix material owing to its fundamentally high hydrophilicity and swellability. In addition, the biomaterial according to the invention has high porosity, as a result of the freeze-drying process, which additionally facilitates the passage of liquids. It is an additional advantage that the collagen biomaterial according to the invention per se already have a positive influence on the wound healing process, in particular also because of the releasable soluble collagen, RGD peptide and protein constituents contained therein.

The bioactive collagen biomaterial composition of the invention is frozen, lyophilized and may be further cross-linked in some embodiments. Cross-linking serves to increase the mechanical stability of the biomaterial and to reduce its rate of resorption by the body. In some aspects of the invention cross-linking is not required. Cross-linking can be achieved chemically with aldehydes, (e.g., formaldehyde, glyoxal, glutaraldehyde, or starchaldehyde, or the like), diisocyanates (e.g., hexamethylenediisocyanate), carbodiimides (e.g., [1-ethyl-3(3-dimethyl aminopropyl)carbodiimide]-hydrochloride (EDC)), or succinimides (e.g., N-hydroxysuccinimide (NHS)) polyaziridines, diglycidyl ethers and mixtures thereof.

Still in other embodiments of the invention, the bioactive collagen biomaterial can be made without the use of chemical cross-linking agents. Instead, cross linking can be achieved by the thermodynamically endothermic condensation (dehydration) raction under heat and vaccum known as dehydrothermal crosslinking (DHT). DHT can be used as the denaturing effect of DHT processing at temperatures and conditions denature and/or gelatinizes native collagen in a manner to keep an adequate amount of physical properties but also enough denaturing to expose RGD motifs. Thus in the manufacture of the bioactive collagen biomaterial of the present invention, the collagen, whether denatured or not, is desirably chemically stabilized by a process known as crosslinking. Crosslinking can also be achieved by many methods well known to those in art. In this invention, the thermodynamically unfavourable endothermic condensation (dehydration) reaction under heat and vacuum, known as dehydrothermal crosslinking (DHT) is a desired method of crosslinking as it leads to denaturation of the triple helical structure of native collagen and exposure of cryptic RGD moieties. The use of DHT is effected at temperatures, pressures and times in order to effect exposure of RGD motifs while still maintaining some structural integrity to the collagen such that it can form a biomaterial for use in a variety of clinical applications. DHT is done to reduce moisture content to cross link, but enough moisture is provided to denature the collagen to expose the RGD motif. Suitable temperatures are from about 45° C. to about 180° C. for up to several hours at suitable vacuum of about 10-5 mm of mercury. Moisture content is desired from about at least 1%, at least about 2%, at least about 3% or more by weight of final biomaterial.

While referencing no particular theory, the biomaterial produced by DHT collagen processing at temperatures above 100° C., when applied to tissue, such as an open wound, acts as a tissue cover that impedes microbial contamination, absorbs wound exudate, and functions as depot for cells within the wound bed, essential biochemical factors, such as enzymes, hormones, amino acids, cell signal molecules, such as RGD, ECM molecules, and cells that promote biological activation effects, such cell migration, remodelling of the ECM, angiogenesis, and wound closure.

In accordance with an embodiment of the invention a bioactive collagen biomaterial comprises native and denatured and hydrolyzed collagen admixed with carboxymethylcellulose, or alginate, and/or biocellulose, and/or synthetic polymers in a single matrix, pad, sponge, film or other configuration having cryptic and non-cryptic RGD tripeptides in varying amounts and native fibrillar collagen in varying amounts, and carboxymethylcellulose, and/or alginate, and/or biocellulose or combinations thereof in various amounts that is not crosslinked and further admixing the antiseptic polyhexamethylne biguanide (PHMB) and at least one metal chelator such as EDTA. The matrix is lyophilized such that it does not contain substantial amounts of solvent and comprises native collagen or a mixture of native and denatured and hydrolyzed collagen, biocompatible polymers, PHMB, EDTA and optional therapeutics or cells.

Further although embodiments of these inventions have been disclosed in the context of certain examples, it will be understood by those skilled in the art that the present inventions extend beyond the specifically disclosed embodiments to other alternative embodiments and/or uses of the inventions and modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect(s) described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. For example, in aspects, certain of the recited components if desired can be explicitly excluded from the compositions and methods described herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Collagen Solutions—Solutions of Collagen Type 1 can be made by any of several methods as is known in the prior art. The collagen solutions can be made in any concentration deemed suitable for the specific purpose as is generally acceptable in the prior art.

Scaffold Fabrication—Scaffolds are produced by freeze-drying a collagen suspension. The preparation of collagen solutions with and without added polymeric materials is generally known (U.S. Pat. Nos. 4,970,298; 4,703,108; 2,559,395; and US 2011/0097402, the disclosures of each are incorporated herein in their entirety).

In brief, collagen scaffolds may be prepared by redissolving freeze-dried 0.6% w/v collagen solution in 0.05M acetic acid or other suitable acid solution. Additives, such as carboxymethylcellulose, chondroitin sulphate, alginate, or other polymeric material may be admixed or blended into the collagen solution. The mixture may be blended or agitated with a blender (7,000-15,000 rpm) at an appropriate temperature ranging from 4° C.-25° C., or above as appropriate, insure adequate mixing in the case of a suspension and additionally degassed under vacuum. The mixture is stored at 4° C. for at least 1 hour to several hours, up to overnight. The solution is freeze-dried in a metal tray (12 cm×12 cm) cooled to −40° C. at 0.9° C./min in a freeze dryer. After freezing ice crystals were removed via sublimation for 17 h at 0° C. and 200 mTorr. This process produces a highly porous sheet of collagen biomaterial. After freeze-drying samples were prepared for DHT processing inside a vacuum oven, 105° C.-180° C. under a vacuum of 0.05 bar. Crosslinking was accomplished by dehydrothermal crosslinking. In dehydrothermal crosslinking, the porous lyophilized foam was dehydrated to reduce the moisture content to the temperature at which crosslinking occurs, at about 1-2% moisture, or about 5-10% moisture or about 15% moisture. The product was subjected to elevated temperatures and/or vacuum conditions until such crosslinking occured. Useful combinations of such conditions include vacuum of at least about $10^{-5}$ mm of mercury, and temperatures of at least about 45° C., being the transition temperature at which native collagen is denatured. It is preferred that effective crosslinking is accomplished by exposure to temperatures of about 115° C. to about 125° C. for periods of about three to about four hours, up to 24 hours. In aspects the crosslinking occurs at temperatures of about 150° C. to about 180° C. for several hours.

Example 2

Haugh et al. (2009) described the fabrication of collagen-GAG scaffolds, the description of which is incorporated herein by reference in its entirety. Bioactive biomaterials of the invention were produced by freeze-drying a collagen-GAG slurry.23 To prepare the slurry, type I bovine collagen (Integra Life Sciences, Plainsboro, N.J.), chondroitin-6-sulphate (Sigma-Aldrich Chemical Co., St. Louis, Mo.) and 0.05 M glacial acetic acid were blended together at 15,000 rpm using an overhead blender (Ultra Turrax T18, IKA-Works Inc., Wilmington, N.C.). Blending was carried out in a reaction vessel, which was maintained at 4° C. using a circulation cooling system (WKL 230, Lauda, Germany). The resulting collagen-GAG slurry contained 0.5% (w/v) collagen and 0.044% (w/v) chondroitin-6-sulfate. The slurry was then degassed in vacuum desiccator for 60 min to remove air bubbles from the solution. Briefly, 67.25 ml of the collagen-GAG slurry was pipetted into a stainless steel pan (5×5 in, grade 304 SS). The tray was placed onto the freeze-dryer shelf (Advantage EL, VirTis Co., Gardiner, N.Y.) and cooled to −40° C. at 0.9° C./min. Previous work has found that this freezing protocol produces scaffolds with a mean pore size of about 96 μm. Once freezing was complete, the ice crystals were removed via sublimation for 17 h at 0° C. and 200 mTorr. This process produced a highly porous sheet of CG scaffold (biomaterial). DHT treatment was carried by placing the scaffolds in an aluminium foil packet inside a vacuum oven (Vacucell 22, MMM, Germany) under a vacuum of 0.05 bar. To determine the effect of DHT parameters on CG scaffold properties, exposure period and crosslinking temperature were varied. Exposure period was varied from 24 h to 120 h, at 24 h intervals, and four crosslinking temperatures were used: 105° C., 120° C., 150° C. and 180° C. Sterilization typically occurs after exposure of about three to about four hours at 160° C. or for periods of from about 24 hours to about forty hours at a temperature of about 125° C. Different crosslinking temperatures, greater than 90° C. were used, while crosslinking temperatures in the range of 100° C.-120° C. are preferred and crosslinking temperatures of 120° C. to 150° C. are more preferred, and crosslinking temperatures of 170° C.-180° C. are most preferred. The biomaterials of the invention as made herein contain 25% denatured collagen after treatment at 105° C. for 24 h, and 60% denatured collagen after extensive treatment at 180° C. for 120 h. Biomaterials having 60% denatured collagen is a desired embodiment of the invention. Testing conducted demonstrates the biomaterial of the invention exhibits desired cellular effects.

The above-disclosed subject matter is to be considered illustrative, and not restrictive, and the appended claims are intended to cover all such modifications, enhancements, and other embodiments that fall within the true scope of the present invention. Thus, to the maximum extent, the scope of the present invention is to be determined by the broadest permissible interpretation of the following claims and their equivalents, and shall not be restricted or limited by the foregoing detailed description.

The invention claimed is:

1. A bioactive collagen biomaterial for accelerated wound healing while impeding microbial contamination, said biomaterial consisting essentially of:
   a) a blend of native collagen, hydrolyzed collagen and denatured collagen having RGD motifs exposed in varying amounts by dehydrothermal treatment (DHT) thereof, the DHT exposing previously cryptic RGD motifs in the native collagen while maintaining sufficient triple helix structure of the native collagen for physical support, wherein the exposed RGD motifs are available for cellular activation to promote wound healing at a wound site;
   b) polyhexamethylene biguanide (PHMB) in an amount of about 0.001% to about 5% by weight; and
   c) ethylenediaminetetraacetic acid (EDTA) in an amount of about 0.001% to about 5% by weight,
   wherein the bioactive collagen biomaterial is degraded at the wound site at different rates exposing further RGD motifs in the biomaterial due to different susceptibilities of the native collagen, the hydrolyzed collagen and the denatured collagen to proteolytic enzymes present at the wound site;
   wherein the bioactive collagen biomaterial impedes microbial contamination at the wound site; and wherein said bioactive collagen biomaterial is flexible, porous and lyophilized.

2. The biomaterial of claim 1, wherein the native collagen is fibrillar type 1 collagen.

3. The biomaterial of claim 1, wherein the biomaterial is at least 55% by weight collagen.

4. The biomaterial of claim 1, wherein the biomaterial is absent of chemical cross-linking.

5. The biomaterial of claim 1, wherein the biomaterial has a moisture content of from about 1% up to about 15% or about 2% up to about 15%.

6. The biomaterial of claim 1, wherein the biomaterial is porous with pore sizes in the range of from about 0.1 μm to about 500 μm.

7. The biomaterial of claim 1, further consisting of one or more of a plasticizer, chelator, peptide, growth factor, steroid, cells, structure forming proteins, and biocompatible polymer selected from the group consisting of carboxymethylcellulose, cellulose, hyaluronic acid, chondroitin sulphate, chitosan, and mixtures thereof.

8. The biomaterial of claim 7, wherein the plasticizer is selected from the group consisting of glycerol, polyethylene glycol and sorbitol in an amount of about 1% to about 20% by weight.

9. The biomaterial of claim 8, wherein the structure forming proteins are matrix proteins or extracellular matrix constituents.

10. The biomaterial of claim 9, wherein the structure forming proteins are selected from the group consisting of elastin, elastin hydrolysates, glycosaminoglycans, proteoglycans, fibrin, fibronectin, and glucans; wherein the glycosaminoglycans are selected from the group consisting of heparan sulfate, chondroitin sulfate, dermatan sulfate, keratan sulfate, heparin and hyaluronic acid; and wherein the proteoglycans are selected from the group consisting of aggrecan, fibromodulin, decorin, biglycan, versican, perlecan, high-density basal membrane proteoglycan, syndecan, and serglycinel.

11. The biomaterial of claim 1, wherein the biomaterial is in a form selected from the group consisting of pads, scaffolds, films, tissue coverings, surgical implants, dental implants, bone coverings, topical would dressings, tissue barriers, organ barriers, and sponges.

12. The biomaterial of claim 1, wherein the biomaterial forms part of an occlusive device comprising an occlusive structure and the biomaterial, wherein the occlusive device is a polymer film that is gas and liquid permeable, or is fitted with pores or holes or slits to make it gas and liquid permeable.

13. The biomaterial of claim 1, wherein the biomaterial is fabricated with at least one other material selected from the group consisting of metals, polymer sheets, films, threads, membranes or meshes of silicone, polyurethane, polyethylene, polymeric fibers, nylon, silk, cellulose and combinations thereof.

14. The biomaterial of claim 1, wherein said DHT is carried out at a temperature of at least 100° C.

15. The biomaterial of claim 14, wherein said DHT is carried out at a temperature of 100° C.-120° C.

16. The biomaterial of claim 14, wherein said DHT is carried out at a temperature of 120° C.-150° C.

17. The biomaterial of claim 14, wherein said DHT is carried out at a temperature of 170° C.-180° C.

18. The biomaterial of claim 1, wherein said DHT is carried out under a vacuum of about 0.05 bar.

19. The biomaterial of claim 1, wherein said DHT is carried out for up to 24 hours.

20. The biomaterial of claim 1, wherein said DHT is carried out for up to 120 hours.

21. The biomaterial of claim 1, wherein the biomaterial comprises up to 60% denatured collagen.

* * * * *